US00PP36016P2

(12) United States Plant Patent
Barnes

(10) Patent No.: US PP36,016 P2
(45) Date of Patent: Jul. 16, 2024

(54) ***PETUNIA* PLANT NAMED 'WNPETSTPER23'**

(50) Latin Name: ***Petunia* X *hybrida***
Varietal Denomination: WNPETSTPER23

(71) Applicant: Brent D. Barnes, Riverside, CA (US)

(72) Inventor: Brent D. Barnes, Riverside, CA (US)

(73) Assignee: WINGEN, LLC, Mustang Ridge, TX (US)

( * ) Notice: Subject to any disclaimer, the term of this patent is extended or adjusted under 35 U.S.C. 154(b) by 0 days.

(21) Appl. No.: 18/129,049

(22) Filed: Mar. 30, 2023

(51) Int. Cl.
*A01H 5/02* (2018.01)
*A01H 6/82* (2018.01)

(52) U.S. Cl.
USPC ..... Plt./356.13

(58) Field of Classification Search
USPC ..... Plt./356.13, 356.21
CPC ..... A01H 5/02; A01H 5/00; A01H 6/82
See application file for complete search history.

(56) References Cited

PUBLICATIONS

Eason Horticultural Resources New Variety Lookbook 2022 Annual Report, retrieved on Jul. 31, 2023 at https://ehrnet.com/wp-content/uploads/2022/06/EHR-New-Variety-Lookbook-CAST-2022-comp.-6-6-22-1.pdf, one cover page, 1, 18, 2 back cover pages. (Year: 2022).*

* cited by examiner

*Primary Examiner* — June Hwu
(74) *Attorney, Agent, or Firm* — C. Anne Whealy

(57) ABSTRACT

A new and distinct *Petunia* plant named 'WNPETSTPER23', characterized by its upright to outwardly spreading and mounding to eventually trailing and decumbent plant habit; vigorous growth habit and rapid growth rate; freely branching habit; dense and bushy plant form; early and freely flowering habit; single-type flowers that are dark pink in color with bright yellowish green-colored star-shaped centers; and excellent container and garden performance.

2 Drawing Sheets

Figure 1:
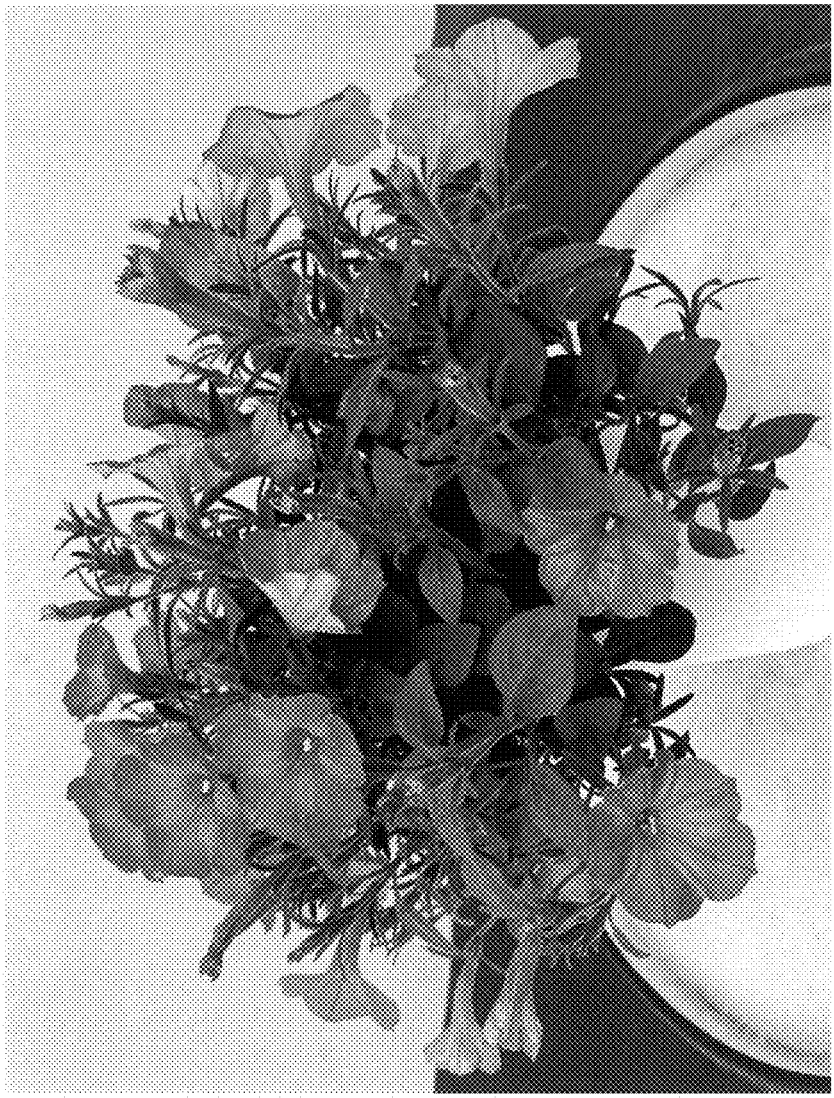

Botanical designation: *Petunia* X *hybrida.*
Cultivar denomination: 'WNPETSTPER23'.

BACKGROUND OF THE INVENTION

The present invention relates to a new and distinct cultivar of *Petunia* plant, botanically known as *Petunia* X *hybrida* and hereinafter referred to by the name 'WNPETSTPER23'.

The new *Petunia* plant is a product of a planned breeding program conducted by the Inventor in Bonsall, California. The objective of the breeding program is to create new vigorous, freely-branching and uniformly mounding *Petunia* plants with early and freely flowering habit, attractive flowers and good garden performance.

The new *Petunia* plant originated from a cross-pollination made by the Inventor on Nov. 12, 2017 in Bonsall, California of a proprietary selection of *Petunia* X *hybrida* identified as code number 17PB319-02, not patented, as the female, or seed, parent with a proprietary selection of *Petunia* X *hybrida* identified as code number 15P931-02, not patented, as the male, or pollen, parent. The new *Petunia* plant was discovered and selected by the Inventor as a single flowering plant within the progeny of the stated cross-pollination in a controlled greenhouse environment in Bonsall, California on Aug. 22, 2018.

Asexual reproduction of the new *Petunia* plant by vegetative terminal cuttings in a controlled greenhouse environment in Bonsall, California since Aug. 28, 2018 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'WNPETSTPER23'. These characteristics in combination distinguish 'WNPETSTPER23' as a new and distinct *Petunia* plant:

1. Upright to outwardly spreading and mounding to eventually trailing and decumbent plant habit.
2. Vigorous growth habit and rapid growth rate.
3. Freely branching habit; dense and bushy plant form.
4. Early and freely flowering habit.
5. Single-type flowers that are dark pink in color with bright yellowish green-colored star-shaped centers.
6. Excellent container and garden performance.

Plants of the new *Petunia* can be compared to plants of the female parent selection. In side-by-side comparisons, plants of the new *Petunia* differ primarily from plants of the female parent selection in the following characteristics:

1. Plants of the new *Petunia* are more vigorous than plants of the female parent selection.
2. Plants of the new *Petunia* flower earlier than plants of the female parent selection.
3. Flowers of plants of the new *Petunia* are dark pink in color with bright yellowish green-colored star-shaped centers whereas flowers of plants of the female parent selection are intense purple in color.

Plants of the new *Petunia* can be compared to plants of the male parent selection. In side-by-side comparisons, plants of the new *Petunia* differ primarily from plants of the male parent selection in the following characteristics:

1. Plants of the new *Petunia* are more upright than and not as trailing as plants of the male parent selection.
2. Plants of the new *Petunia* have larger flowers than plants of the male parent selection.
3. Flowers of plants of the new *Petunia* are dark pink in color with bright yellowish green-colored star-shaped centers whereas flowers of plants of the male parent selection are purple in color.

Plants of the new *Petunia* can be compared to plants of *Petunia sensu wijsman* 'DCAS303', disclosed in U.S. Plant Pat. No. 26,888. In side-by-side comparisons, plants of the new *Petunia* differ primarily from plants of 'DCAS303' in the following characteristics:

1. Plants of the new *Petunia* are more upright and denser than plants of 'DCAS303'.
2. Flowers of plants of the new *Petunia* are dark pink in color with bright yellowish green-colored star-shaped centers whereas flowers of plants of 'DCAS303' are yellow to blush pink in color.
3. Plants of the new *Petunia* have better container and garden performance than plants of 'DCAS303'.

Plants of the new *Petunia* can also be compared to plants of *Petunia* x *hybrida* 'Sanguna® Patio Melon Morn', not patented. In side-by-side comparisons, plants of the new *Petunia* differ primarily from plants of 'Sanguna® Patio Melon Morn' in the following characteristics:

1. Plants of the new *Petunia* are denser than and not as compact as plants of 'Sanguna® Patio Melon Morn'.
2. Flowers of plants of the new *Petunia* are dark pink in color with bright yellowish green-colored star-shaped centers whereas flowers of plants of 'Sanguna® Patio Melon Morn' are coral in color with white-colored centers.
3. Plants of the new *Petunia* have better container and garden performance than plants of 'Sanguna® Patio Melon Morn'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph on the first sheet (FIG. 1) is a side perspective view of a typical flowering plant of 'WNPETSTPER23' grown in a container.

Figure 2:
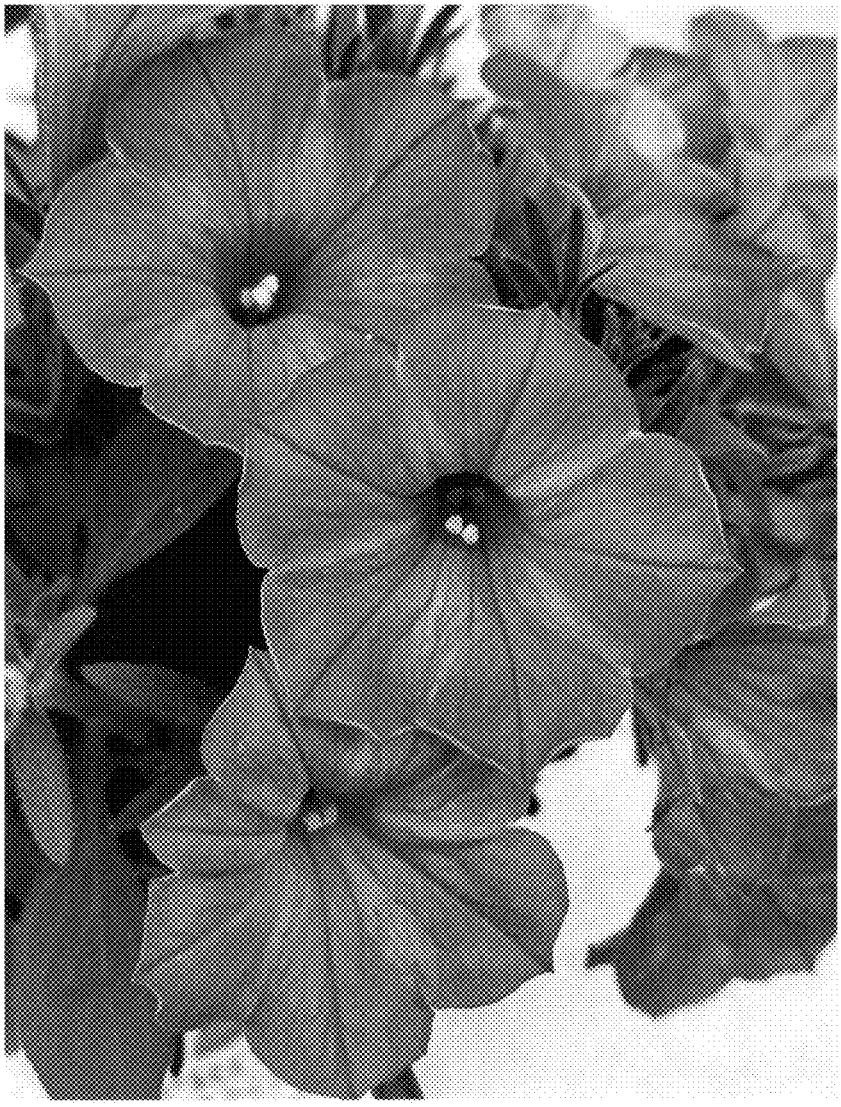

The photograph on the second sheet (FIG. 2) is a close-up view of a typical flowering plant of 'WNPETSTPER23 '.

DETAILED BOTANICAL DESCRIPTION

The aforementioned photographs and following observations and measurements describe plants grown during the summer in 740-ml containers in an acrylic-covered greenhouse in Carlton, Michigan and under cultural practices typical of commercial *Petunia* production. During the production of the plants, day temperatures ranged from 18 C to 32 C and night temperatures ranged from 18 C to 24 C. Plants were pinched two weeks after planting and were five weeks from planting rooted cuttings when the photographs and description were taken. In the following description, color references are made to The Royal Horticultural Society Colour Chart, 2015 Edition, except where general terms of ordinary dictionary significance are used.

Botanical classification: *Petunia* X *hybrida* 'WNPETSTPER23'.

Parentage:

*Female, or seed, parent*.—Proprietary selection of *Petunia* X *hybrida* identified as code number 17PB319-02, not patented.

*Male, or pollen, parent*.—Proprietary selection of *Petunia* X *hybrida* identified as code number 15P931-02, not patented.

Propagation:

*Type*.—Terminal vegetative cuttings.

*Time to initiate roots, summer*.—About three to four days at ambient temperatures about 28 C.

*Time to initiate roots, winter*.—About five to seven days at ambient temperatures about 20 C.

*Time to produce a rooted plant, summer*.—About three or four weeks at ambient temperatures about 28 C.

*Time to produce a rooted plant, winter*.—About four to five weeks at ambient temperatures about 20 C.

*Root description*.—Fine, fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Upright to outwardly spreading and mounding to eventually trailing and decumbent plant habit; freely branching habit with about eight to ten primary lateral branches with secondary laterals developing potentially at every node, dense and bushy plant form; pinching enhances development of lateral branches; vigorous growth habit and rapid growth rate.

*Plant height*.—About 15 cm.

*Plant diameter* (*area of spread*).—About 42 cm.

*Lateral branches*.—Length: About 26 cm. Diameter: About 2.5 mm. Internode length: About 1.75 cm. Strength: Moderately strong; flexible, not brittle. Aspect: Initially upright then outwardly spreading to trailing and decumbent. Texture and luster: Densely pubescent; matte to slightly glossy. Color, developing and developed: Close to 144A.

Leaf description:

*Arrangement*.—Alternate before flowering; opposite after flowers develop; leaves simple.

*Length*.—About 3.1 cm.

*Width*.—About 1.7 cm.

*Shape*.—Elliptic.

*Apex*.—Acute.

*Base*.—Cuneate.

*Margin*.—Entire, not undulate.

*Texture and luster, upper and lower surfaces*.—Moderately pubescent, pubescence, minute; matte.

*Venation pattern*.—Pinnate, arcuate.

*Color*.—Developing leaves, upper and lower surfaces: Close to 144A. Fully developed leaves, upper surface: Close to NN137A to NN137B; venation, close to 144A. Fully developed leaves, lower surface: Close to 138A; venation, close to 144A.

*Petioles*.—Length: About 7 mm. Diameter: About 2.5 mm. Strength: Strong, flexible. Texture and luster, upper and lower surfaces: Densely pubescent; matte to slightly glossy. Color, upper and lower surfaces: Close to 144A.

Flower description:

*Flower type and flowering habit*.—Single terminal and axillary salverfotm flowers; flowers face mostly upward to outwardly; freely flowering habit with about 65 developing flowers and open flowers per plant.

*Natural flowering season*.—Long day responsive; long flowering period, plants flower from early spring until frost in the autumn, flowering continuous during this period; early flowering habit, plants begin flowering about four weeks after planting rooted young plants.

*Flower longevity on the plant*.—Depending on temperature, about one to two weeks; petals not persistent, and sepals, persistent.

*Fragrance*.—None detected.

*Flower buds, before showing petal color*.—Length: About 2 cm. Diameter: About 4 mm. Shape: Oblong, elongate. Texture and luster: Pubescent; matte to slightly glossy. Color, developing sepals: Close to 144A.

*Flower diameter*.—About 4 cm.

*Flower depth* (*height*).—About 3.75 cm.

*Throat diameter*.—About 7.5 mm.

*Tube length*.—About 3 cm.

*Tube diameter, distally*.—About 8 mm.

*Tube diameter, proximally*.—About 2 mm.

*Petals*.—Quantity and arrangement: Five petals fused in a single salverform whorl. Petal lobe length (from throat): About 1.75 cm. Petal lobe width: About 1.8 cm. Petal lobe shape: Roughly spatulate. Petal lobe apex: Broadly obtuse and cuspidate. Petal lobe margin: Entire; moderately undulate. Petal lobe texture and luster, upper surface: Smooth, glabrous; velvety; matte. Petal lobe texture and luster, lower surface: Smooth, glabrous; slightly glossy. Throat texture and luster: Smooth, glabrous; slightly glossy. Tube texture and luster: Moderately pubescent; matte. Color: When opening and fully opened, upper surface: Close to 58A to 58B; central star-shape pattern, close to between 3A and 154A; primary venation, close to 144A, and lateral venation, close to 58A to 58B, venation moderately to strongly conspicuous; color does not change with subsequent development. When opening and fully opened, lower surface: Close to 69B; venation, close to 144A; color does not change with subsequent development. Flower throat (inside): Close to N144B; venation, close to 144A. Flower tube (outside): Close to 144A; venation, close to 144A.

*Sepals*.—Quantity and arrangement: Five sepals fused in a single star-shaped whorl. Length: About 1.5 cm. Width: About 3 mm. Shape: Linear. Apex: Acute. Margin: Entire. Texture and luster, upper surface: Sparsely to moderately pubescent; matte to slightly glossy. Texture and luster, lower surface: Moderately pubescent; matte. Color: When opening and fully developed, upper surface: Close to 144A. When opening and fully developed, lower surface: Close to 144A.

*Peduncles*.—Length: About 3 cm. Width: About 1 mm. Strength: Moderately strong; wiry and flexible, not brittle. Angle: About 45 degrees from the stem axis. Texture and luster: Densely pubescent; slightly glossy. Color: Close to 144A.

*Reproductive organs*.—Stamens: Quantity per flower: About five. Filament length: About 2.1 cm. Filament color: Close to 157A to 157B. Anther length: About 1 mm. Anther shape: Bi-lobed. Anther color: Close to 157A. Pollen amount: None observed. Pistils: Quantity per flower: One. Pistil length: About 2.2 cm. Style length: About 2.1 cm. Style color: Close to 144C. Stigma diameter: About 1 mm. Stigma shape: Round. Stigma color: Close to 144A. Ovary color: Close to 144A.

*Seeds and fruits*.—To date, seed and fruit development has not been observed on plants of the new *Petunia*.

Pathogen & pest resistance: To date, plants of the new *Petunia* have not been noted to be resistant to pathogens or pests common to *Petunia* plants.

Garden performance: Plants of the new *Petunia* have been observed to have excellent garden performance and have been observed to tolerate rain, wind and temperatures ranging from about 1 C to about 35 C.

It is claimed:

1. A new and distinct *Petunia* plant named 'WNPETSTPER23' as illustrated and described.

* * * * *